US00PP10404P

United States Patent [19]

Jessel, Jr.

[11] Patent Number: Plant 10,404

[45] Date of Patent: May 19, 1998

[54] CARNATION PLANT NAMED 'CFPC WHISPER'

[75] Inventor: Walter H. Jessel, Jr., Gonzales, Calif.

[73] Assignee: California Florida Plant Co., L.P., Salinas, Calif.

[21] Appl. No.: 749,922

[22] Filed: Nov. 12, 1996

[51] Int. Cl.[6] ..... A01H 5/00

[52] U.S. Cl. ..... Plt./70.2

[58] Field of Search ..... Plt./70.2

[56] References Cited

U.S. PATENT DOCUMENTS

P.P. 9,267 8/1995 Jessel, Jr. ..... Plt./70.5

*Primary Examiner*—Howard J. Locker

*Attorney, Agent, or Firm*—Christie, Parker & Hale, LLP

[57] ABSTRACT

A new variety of carnation pot plant producing sprays of white striped picotee violet flowers.

1 Drawing Sheet

BACKGROUND OF THE INVENTION

The present invention relates to a new and distinct dwarf variety of carnation plant which was originated by me from a cross made in a controlled breeding program. The female parent is 'CFPC Cotillion' (U.S. Plant Pat. No. 9,267). and the male parent is undistributed and unpatented seedling identified as No. 920573. The varietal denomination of this new carnation is 'CFPC Whisper'.

SUMMARY OF THE INVENTION

The new variety is a true dwarf carnation suitable for growing in 4 to 4 ½ -inch pots (1 plant, 1 pinch, one plant per pot and a single pinch), tolerant to temperatures of about 10 to 120° F., with a keeping quality of about 3 to 4 weeks. Flower buds open from green bud to maturity with moderate light. No disease problems have been observed as yet.

If planted outdoors, the new variety will continue to recycle growth and blooms. It appears to be perennial in nature in most sections of the country.

In addition to the foregoing, the new variety exhibits superior resistance to soil borne diseases such as *F. oxysporum, strains* 1 and 2, and F. graminearum, and root-rots such as damping off, water molds, and the like.

Asexual reproduction by propagation by side shoot cuttings of the new variety as performed in Salinas, Calif., shows that the foregoing and other distinguishing characteristics come true to form and are established and transmitted through succeeding propagations.

COMPARISON WITH PARENT

In contrast to the new variety, 'CFPC Cotillion' produces flowers having a lavender/pink flower color on a more compact plant. Seedling No. 920573 produces lavender flowers with red-purple markings on all petals and an undesirably large amount of pollen.

BRIEF DESCRIPTION OF ILLUSTRATION

The accompanying illustration shows typical specimens of the flowers and foliage of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart. Phenotypic expression and color descriptions may vary depending upon varying environmental, seasonal and cultural conditions.

The information provided herein is based on observations of plants grown inside commercial greenhouses at Salinas, California. The height of plant and flower and foliage size are established as an average using standard commercial cultural practices. Where terms such as average, normal, ordinary, etc., are used, the characteristics so described are not considered distinguishing.

Name: 'CFPC Whisper'.

Classification:

*Botanical.*—Dianthus caryophyllus.

*Commercial.*—Carnation, greenhouse type, suitable for production as a pot variety producing flower sprays.

Parentage:

*Female parent.*—CFPC 'Cotillion'.

*Male parent.*—Seedling No. 920573.

1. Plant:

*Height.*—Pinched plants are about 7 to 9 inches tall.

*Growing habit.*—Herbaceous, semi-upright.

*Blooming habit.*—As a pot spray type.

*Blooming season.*—Year round.

*Rooting time.*—About 17 days.

*Mutation prone.*—No.

*Disease resistance.*—Good.

*Temperature tolerance.*—Wide range.

*Breaking action.*—Excellent, approximately 8 per plant.

2. Foliage:

*Color.*—Upper side: Near 138A. Lower side: Near 139B.

*Size.*—About 4 inches long, about ¼ inches wide.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Near 137A.

3. Bud:

*Shape.*—Ovoid.

*Color.*—Near 137B.

*Length.*—About 1 inch.

*Diameter.*—About ⅜ inch.

4. Calyx:
   *Number of sepals.*—About 5.
   *Length.*—About ½ inch.
   *Width.*—About 3/16 inch.
   *Color.*—Outside—Near 144A. Inside—Near 143C.
5. Bloom:
   *Shape.*—Round.
   *Size.*—Diameter average: About 1¾ inches. Depth average: About ⅞ inch.
   *Borne.*—As a spray, approximately 6 to 8 blooms per flowering stem, stem length about 7½ to 8½ inches.
   *Color.*—General tonality: White striped and picotee violet. Upper side: Whiter than 155D with picotee red-purple edge. Lower side: Whiter than 155D with picotee red-purple edge. Center: Whiter than 155D. Outer petals: 71C picotee edge and stripes on white background.
   *Keeping quality.*—Entire bloom flush about 3 weeks.
   *Fragrance.*—None.
6. Petals:
   *Number.*—About 20.
   *Outer petals.*—Length; About 1½ inches. Width: About ¾ inch.
   *Central petals.*—Length: About 1⅜ inches. Width: About ½ inch.
   *Texture.*—Smooth.
   *Form.*—Fan shaped.
   *Appearance.*—Shiny petal edge smooth.
7. Reproductive organs:
   *Stamens.*—None (male sterile).
   *Pistil.*—Number: About 1. Color: Whiter than 155D. Length: About 1⅜ inch.
   *Stigma.*—Number: About 2 to 3 lobes. Color: Whiter than 155D.
   *Ovary.*— Shape: Conical. Color: Base—Near 154C. Body Near—Near 145B. Apex—Near 19D.
   *Fertility.*—Female: Good. Male: Sterile.

I claim:

1. A new and distinct variety of carnation plant substantially as shown and described.

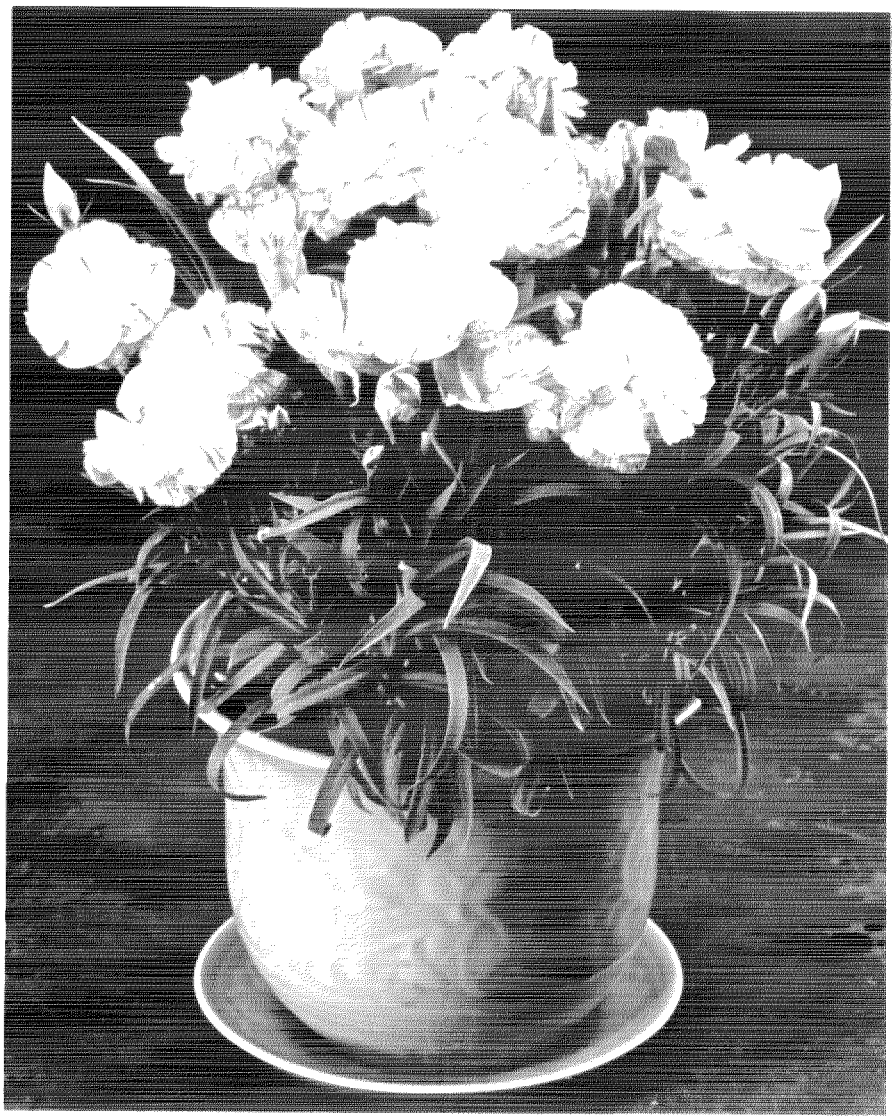

* * * * *